(12) United States Patent
Stevenson et al.

(10) Patent No.: US 10,604,491 B2
(45) Date of Patent: *Mar. 31, 2020

(54) CATALYSIS OF DIKETOPIPERAZINE SYNTHESIS

(71) Applicant: MannKind Corporation, Westlake Village, CA (US)

(72) Inventors: John J. Stevenson, Bronx, NY (US); Destardi Moye-Sherman, Newburgh, NY (US)

(73) Assignee: Mannkind corporation, Westlake Village, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/151,797

(22) Filed: Oct. 4, 2018

(65) Prior Publication Data

US 2019/0031621 A1    Jan. 31, 2019

Related U.S. Application Data

(60) Division of application No. 15/698,431, filed on Sep. 7, 2017, now Pat. No. 10,112,910, which is a continuation of application No. 15/097,124, filed on Apr. 12, 2016, now Pat. No. 9,796,688, which is a continuation of application No. 14/266,632, filed on Apr. 30, 2014, now Pat. No. 9,346,766, which is a continuation of application No. 13/422,989, filed on Mar. 16, 2012, now Pat. No. 8,748,609, which is a division of application No. 12/633,673, filed on Dec. 8, 2009, now Pat. No. 8,202,992, which is a continuation of application No. 11/208,087, filed on Aug. 19, 2005, now Pat. No. 7,709,639.

(60) Provisional application No. 60/603,340, filed on Aug. 20, 2004.

(51) Int. Cl.
*C07D 241/08* (2006.01)
*B01J 27/16* (2006.01)

(52) U.S. Cl.
CPC ............ *C07D 241/08* (2013.01); *B01J 27/16* (2013.01)

(58) Field of Classification Search
CPC ................................ C07D 241/08; B01J 27/16
See application file for complete search history.

(56) References Cited

U.S. PATENT DOCUMENTS 7,709,639 B2 *   5/2010   Stevenson ................ B01J 27/16
                                                            544/385
9,346,766 B2 *   5/2016   Stevenson ................ B01J 27/16
9,796,688 B2 *  10/2017   Stevenson ................ B01J 27/16

* cited by examiner

*Primary Examiner* — Erich A Leeser
(74) *Attorney, Agent, or Firm* — Withers Bergman LLP

(57) ABSTRACT

Provided is a method for the synthesis of N-protected 3,6-bis-[4-aminobutyl]-2,5-diketopiperazine including the step of heating a solution of ε-amino protected lysine in the presence of a catalyst selected from the group consisting of sulfuric acid, phosphoric acid, and phosphorus pentoxide.

8 Claims, 5 Drawing Sheets

CATALYSIS OF DIKETOPIPERAZINE SYNTHESIS

RELATED APPLICATIONS

The present application is a divisional of U.S. patent application Ser. No. 15/698,431, filed on Sep. 7, 2017, which is a continuation of U.S. patent application Ser. No. 15/097,124, filed Apr. 12, 2016, now U.S. Pat. No. 9,796,688, which is a continuation of U.S. patent application Ser. No. 14/266,632, filed Apr. 30, 2014, now U.S. Pat. No. 9,346,766, which is a continuation of U.S. patent application Ser. No. 13/422,989, filed Mar. 16, 2012, now U.S. Pat. No. 8,748,609, which is a divisional of U.S. patent application Ser. No. 12/633,673, filed Dec. 8, 2009, now U.S. Pat. No. 8,202,992, which is a continuation of U.S. patent application Ser. No. 11/208,087, filed Aug. 19, 2005, now U.S. Pat. No. 7,709,639, which claims priority under 35 U.S.C. § 119(e) to U.S. Provisional Patent Application No. 60/603,340, filed Aug. 20, 2004, all of which are incorporated by reference herein in their entirety.

FIELD OF THE INVENTION

This invention is generally in the field of chemical synthesis. More particularly it is related to improved syntheses of N-protected 3,6-bis-[4-aminobutyl]-2,5-diketopiperazines.

BACKGROUND TO THE INVENTION

Drug delivery has been a persistent challenge in the pharmaceutical arts, particularly when a drug is unstable and/or poorly absorbed at the locus in the body to which it is administered. One such class of drugs includes 2,5-diketopiperazines having the general structure of Formula 1.

These 2,5-diketopiperazines have been shown to be useful in drug delivery,

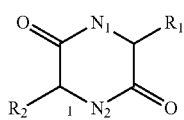

Formula 1 particularly those bearing acidic R groups (see for example U.S. Pat. No. 5,352,461 entitled "Self-assembling diketopiperazine drug delivery system;" U.S. Pat. No. 5,503,852 entitled "Method for making self-assembling diketopiperazine drug delivery system;" U.S. Pat. No. 6,071,497 entitled "Microparticles for lung delivery comprising diketopiperazine;" and U.S. Pat. No. 6,331,318 entitled "Carbon-substituted diketopiperazine delivery system," each of which is incorporated herein by reference in its entirety for all that it teaches regarding diketopiperazines and diketopiperazine-mediated drug delivery). Diketopiperazines can be formed into particles that incorporate a drug or particles to which a drug can be adsorbed. The combination of a drug and a diketopiperazine can impart improved drug stability. The particles can be administered by various routes of administration. As dry powders these particles can be delivered to specific areas of the respiratory system, depending on particle size. The particles can be made small enough for incorporation into intravenous suspension dosage forms. Oral delivery is also possible using a suspension, or as particles pressed into tablets or contained in a capsule. These diketopiperazines can also facilitate absorption of the associated drug.

A conventional step in synthesis of 2,5-diketopiperazines includes the preparation of N-protected 3,6-bis-[4-aminobutyl]-2,5-diketopiperazine by thermal condensation of lysine. Conventional commercial manufacturing processes utilize (N-benzyloxycarbonyl)-lysine (Cbz-L-lysine) to produce 3,6-bis-[(N-benzyloxycarbonyl)-4-aminobutyl]-2,5-diketopiperazine (DKP1). This process entails heating Cbz-L-lysine in m-cresol for 18-22 hours at 160° C.-170° C., and provides DKP1 in an average yield of about 47.5% after recrystallization from glacial acetic acid.

Therefore, it is an object of the present invention to provide improved methods of synthesis for diketopiperazines.

SUMMARY OF THE INVENTION

The present invention provides methods for the synthesis of diketopiperazines using catalysts such that faster reaction times and higher yields are achieved compared to conventional step(s)/method(s). Utilizing the catalyst of the present invention, phosphorus pentoxide, in a cyclocondensation reaction, provides for the synthesis of diketopiperazines of higher yield and higher purity in shorter reaction times over that of conventional step(s)/method(s).

The present invention provides a method for the synthesis of N-protected 3,6-bis-[4-aminobutyl]-2,5-diketopiperazine comprising the step of heating a solution of ε-amino protected lysine in the presence of a catalyst selected from the group consisting of sulfuric acid ($H_2SO_4$), phosphoric acid ($H_3PO_4$), and phosphorus pentoxide ($P_2O_5$).

One embodiment of the present invention provides a method for the synthesis of N-protected 3,6-bis-[4-aminobutyl]-2,5-diketopiperazine wherein the ε-amino protected lysine is (N-benzyloxycarbonyl)-lysine (Cbz-L-lysine) and the product is 3,6-bis-[(N-benzyloxycarbonyl)-4-aminobutyl]-2,5-diketopiperazine (DKP1).

Another embodiment of the present invention provides a method for the synthesis of N-protected 3,6-bis-[4-aminobutyl]-2,5-diketopiperazine wherein the solution is heated to a target temperature of about 160° C. to 170° C. This target temperature is preferably achieved in about 4 to 6 hours.

In yet another embodiment of the present invention a method for the synthesis of N-protected 3,6-bis-[4-aminobutyl]-2,5-diketopiperazine comprising the step of heating a solution of ε-amino protected lysine in the presence of a catalyst is provided wherein synthesis is substantially complete within about 10 hours of reaching a target temperature. More preferably, the synthesis is substantially complete within about 8 hours, 6 hours, 4 hours, 3 hours, or 2 hours of reaching a target temperature. Most preferably, the synthesis is substantially complete within about 1.5 hours of reaching a target temperature.

Another embodiment of the present invention provides a method for the synthesis of N-protected 3,6-bis-[4-aminobutyl]-2,5-diketopiperazine comprising the step of heating a solution of an ε-amino protected lysine, such as (N-benzyloxycarbonyl)-lysine (Cbz-L-lysine), in the presence of a catalyst, such as phosphorus pentoxide, wherein synthesis has a yield of greater than 50%.

Another embodiment of the present invention provides a method for the synthesis of N-protected 3,6-bis-[4-aminobutyl]-2,5-diketopiperazine in the presence of the catalyst phosphorus pentoxide the concentration of phosphorus pentoxide is about 5% to 10%.

These and other objects, advantages and features of the invention will be more fully understood and appreciated by reference to the written specification.

DETAILED DESCRIPTION OF THE INVENTION

The present invention provides methods for the synthesis of diketopiperazines using catalysts such that faster reaction times and higher yields are achieved compared to conventional step(s)/method(s). Utilizing the catalyst of the present invention, phosphorus pentoxide, in a cyclocondensation reaction, provides for the synthesis of diketopiperazines of higher yield and higher purity in shorter reaction times over that of conventional step(s)/method(s).

Figure 1:
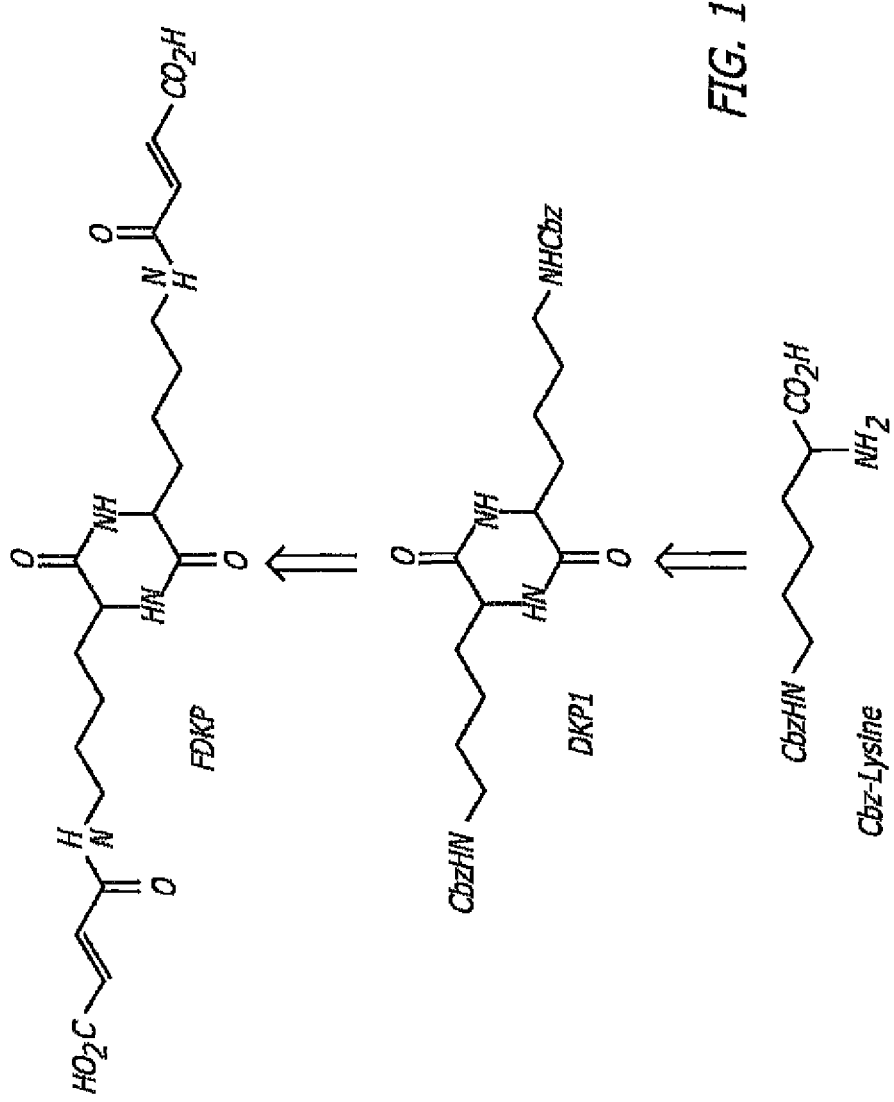
FIG. 1 depicts a flow chart of 2,5-diketo-3,6-di(4-fumarylaminobutyl)piperazine (fumaryl diketopiperazine, FDKP) retrosynthesis according to one aspect of the present invention.
Figure 2:
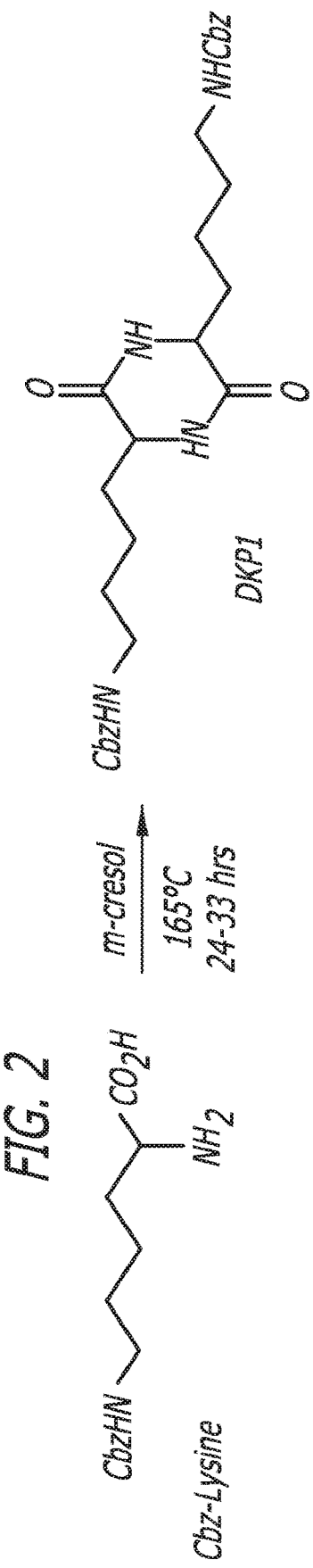
FIG. 2 depicts a flow chart of 3,6-bis-[(N-benzyloxycarbonyl)-4-aminobutyl]-2,5-diketopiperazine (DKP1) synthesis according to one aspect of the present invention.

The conventional synthesis of diketopiperazines useful in drug delivery, such as 2,5-diketo-3,6-di(4-fumarylaminobutyl)piperazine (fumaryl diketopiperazine, FDKP), commonly begins from the thermal cyclocondensation of ε-amino protected lysine, for example (N-benzyloxycarbonyl)-lysine (Cbz-L-lysine) (see FIGS. 1 and 2). The uncatalyzed reaction is lengthy, 18-33 hours, with yields under 50% and in some cases as little as 25%. Such lengthy reactions and relatively low yields lead to undesirably low reactor throughput in industrial applications.

It is appreciated that others have used phosphorous pentoxide ($P_2O_5$) as a catalyst and polyphosphoric acid as the solvent to prepare diketopiperazines. For examples see J. Am. Pharm. Assoc., 1957, 46:391-3, Galinsky et al. wherein the authors describe using polyphosphoric acid with $P_2O_5$ for the preparation of glycine, alanine, leucine, isoleucine and phenylalanine diketopiperazines; see also ARKIVOC 2001 (ii) p. 122-134, Kappe et al. wherein the synthesis of Biginelli dihydropyrimidones using $P_2O_5$ (as the polyphosphate ester) as a cyclocondensation/dehydration reagent is described. Additionally see J. Org. Chem., 1961, 26:2534-6, Erlanger, "Phosphorus pentoxide as a reagent in peptide synthesis." Described therein is $P_2O_5$ (with butanol diethyl hydrogen phosphite) used as a reagent for making a linear dipeptide from protected amino acid fragments. However, it was surprisingly discovered by the present inventors that the reaction conditions and solvents described in the above cited references resulted in degradation of the (N-benzyloxycarbonyl)-lysine starting material and thus were incompatible with the teachings of the present invention. Thus, a catalyst that could speed the reaction and generate higher yields was sought.

One embodiment of the present invention includes the incorporation of a catalyst into the above-noted reaction to increase the speed of the reaction and to generate higher yield percentages of the present invention. The three following reagents were evaluated for their usefulness as catalysts for this dehydrative cyclocondensation reaction: sulfuric acid ($H_2SO_4$), phosphoric acid ($H_3PO_4$), and phosphorus pentoxide ($P_2O_5$) using m-cresol as a solvent. The term "substantially complete" as used herein with regard to the synthesis of the present invention refers to at least about 80% of the starting material being consumed within the prescribed time period. Reactions were carried out with each of the potential catalysts. The consumption of Cbz-L-lysine and the appearance of 3,6-bis-[(N-benzyloxycarbonyl)-4-aminobutyl]-2,5-diketopiperazine (DKP1) were monitored by high performance liquid chromatography (HPLC) at time points throughout this reaction. At selected time points DKP1 was isolated and its yield calculated.

Figure 3:
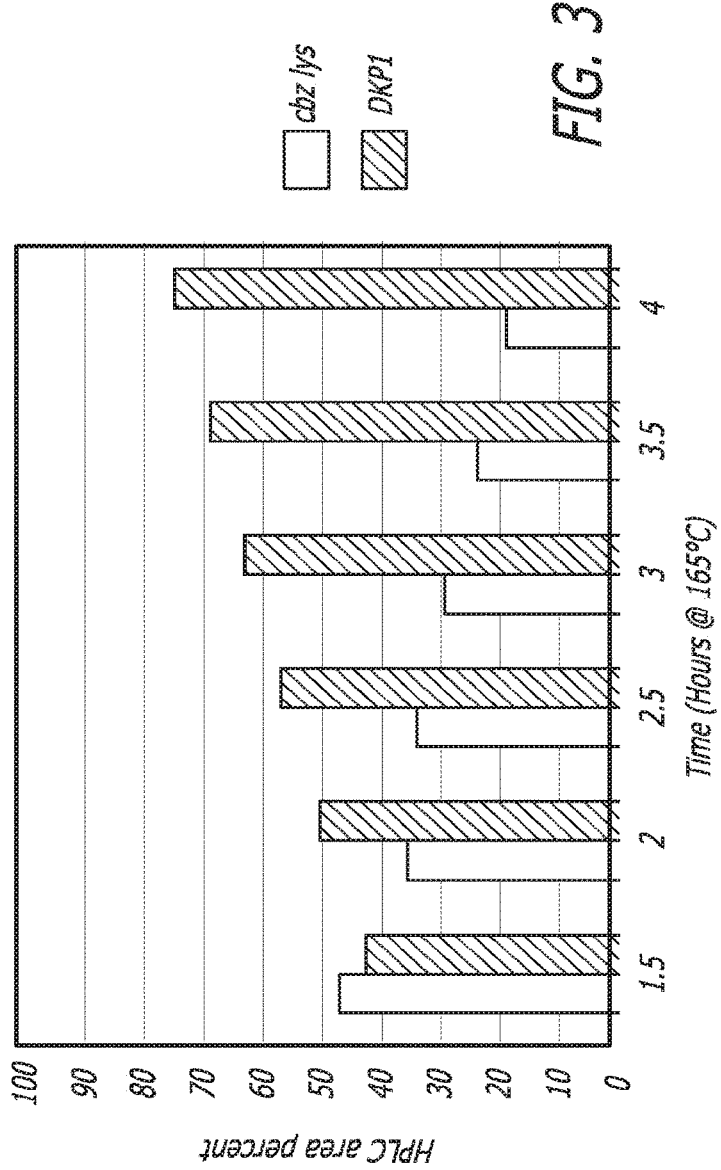
FIG. 3 depicts the conversion of (N-benzyloxycarbonyl)-lysine) Cbz-L-lysine to DKP1 using the sulfuric acid catalysis methods according to one aspect of the present invention.

The presence of sulfuric acid as a catalyst resulted in a yield of about 35%, which is within the range of the uncatalyzed reaction. However, this 35% yield was achieved in only 4 hours (see FIG. 3) as compared to the conventional uncatalyzed reaction times of from about 18 hours to about 33 hours to achieve a similar reaction yield percentage.

Figure 4:
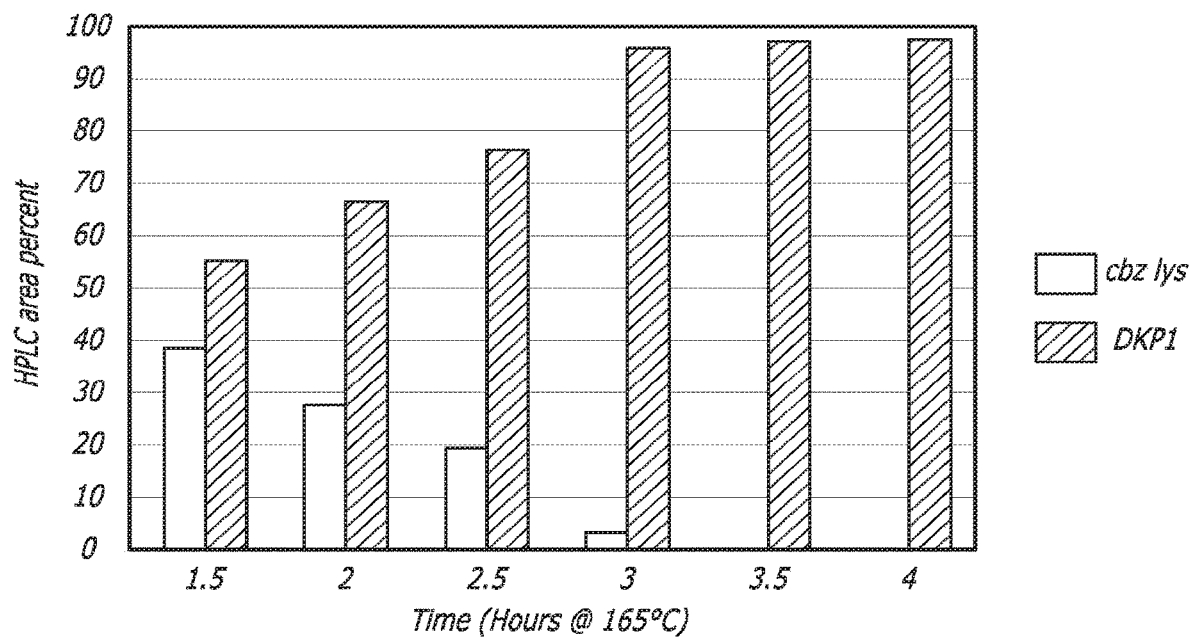
FIG. 4 depicts the conversion of Cbz-L-lysine to DKP1 using the phosphoric acid catalysis methods according to one aspect of the present invention.

The phosphoric acid catalyzed reaction was substantially complete in that it had consumed at least about 80% of the Cbz-L-lysine by about three hours. The DKP1 was stable when evaluated within 4 hours of the reaction and the yield was found to be about 55% (see FIG. 4).

The phosphorus pentoxide catalyzed reaction had consumed about 90% of the Cbz-L-lysine by 1 hour and consumed almost all of the Cbz-L-lysine by about 1.5 hours. At this point, the yield was determined to be about 60% (see FIG. 5). Thus, all three catalysts significantly increased the speed of the reaction; and phosphoric acid and phosphorous pentoxide also increased the yield percentage (see FIG. 6 and Table 1).

TABLE 1

Comparison of catalyzed vs. uncatalyzed DKP1 synthesis

| Catalyst | Temperature ° C. | Time (hours) | % Yield DKP1 |
| --- | --- | --- | --- |
| None | 165 | 24-33 | 25-35 |
| $H_2SO_4$ | 165 | 4 | 35 |
| $H_3PO_4$ | 165 | 4 | 55 |
| $P_2O_5$ | 165 | 1.5 | 60 |

Solvents suitable for use in the reactions of the present invention include, but are not limited to, m-cresol, ethylene glycol, propylene glycol, toluene, xylenes and equivalents known to those skilled in the art. Additionally, as will be apparent to persons skilled in the art, various solvents have different boiling temperatures and polarity and therefore reaction temperatures and reaction times may vary between solvents.

EXAMPLES

Example 1

Phosphorus Pentoxide Catalyzed Synthesis of 3,6-bis[3-(N-benzyloxycarbonyl)aminopropyl]-2,5-diketopiperazine (DKP1a) I

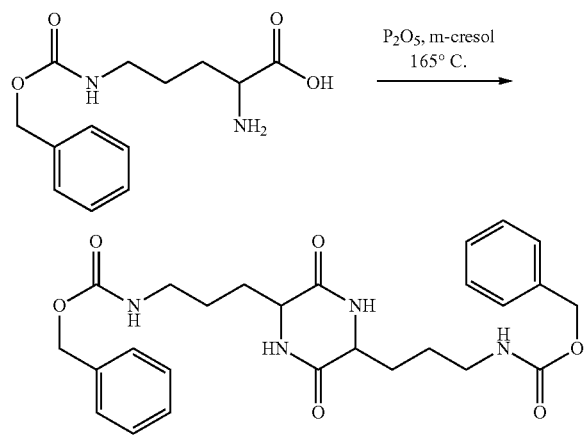

A 4-neck 1-L, round-bottom flask equipped with a mechanical stirrer, thermocouple temperature readout/controller, nitrogen gas inlet, and short-path distillation apparatus was charged with 100 g of Cbz-ornithine, 7.5 g of phosphorus pentoxide, and 300 mL of m-cresol. The stirrer and nitrogen purge were started. The slurry was heated to 165° C.±5° C. After formation of a complete solution (approximately 30-60 minutes), the mixture was held at 165° C. for an additional 60 minutes. The heating mantle was removed and the solution cooled to 50° C. A quench solution was prepared in a 2000-mL beaker consisting of an 80:20 mixture of methanol:water (1000 mL). The warm reaction solution was poured into the stirring methanol (MeOH) solution and the resulting suspension stirred for 30 minutes. The suspension was filtered through a medium porosity sintered glass funnel and the filter cake washed sequentially with 250 mL MeOH, 250 mL deionized water, and 2×250 mL MeOH. The isolated product was dried overnight in a vacuum oven (50° C., 30 inches of mercury). The crude product was recrystallized from acetic acid and dried in a vacuum oven to give 58.5 g (63%) of the desired diketopiperazine.

| Elemental Analysis: | Calc | C 62.89 | H 6.50 | N 11.28 |
|---|---|---|---|---|
| | Found | C 62.15 | H 6.64 | N 11.09 |

$^1$H NMR Analysis: (d$_6$-DMSO):
δ 8.97, 2H (NH); δ 7.28-7.37, 10H (CH); δ 7.08, 2H (NH); δ 5.01, 4H (CH$_2$); δ 3.79, 2H (CH); δ 2.99-3.01, 4H (CH$_2$); δ 1.60-1.70, 4H (CH$_2$); δ 1.46-1.57, 4H (CH$_2$)

Example 2

Phosphorus Pentoxide Catalyzed Synthesis of DKP1 II

Figure 7:
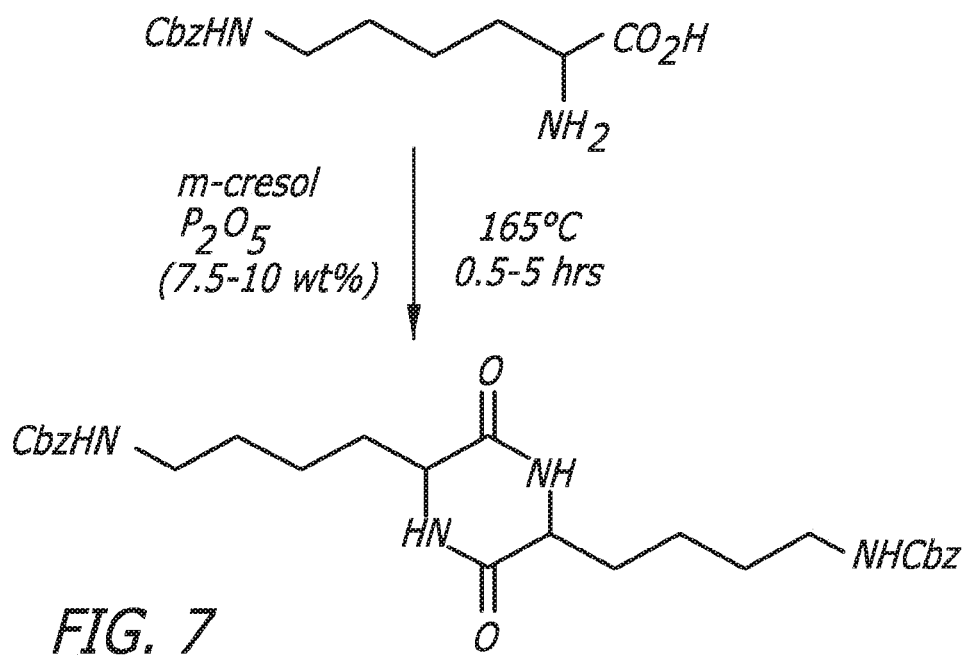
FIG. 7 depicts the reaction sequence of the $P_2O_5$-catalyzed cyclodimerization according to one aspect of the present invention.

A 1-L round bottom flask equipped with a mechanical stirrer, short-path distillation apparatus, a thermocouple temperature read-out/controller, and a nitrogen inlet was charged with Cbz-L-lysine (100 g), m-cresol (200 g) and phosphorus pentoxide (7.5 g). The reaction mixture was stirred, heated to a target temperature of 165° C., and held at temperature for 1.5 hours. See FIG. 7.

After completion of the heating period, the reaction solution was allowed to cool to room temperature (22-25° C.) and quenched with a solution of deionized water (100 mL) and MeOH (400 mL). The resulting suspension was stirred for 30-60 minutes and then filtered through a medium porosity sintered glass funnel. The filter cake was washed sequentially with 250 mL MeOH, 2×250 mL deionized water, and 2×250 mL MeOH.

The wet cake was dried in a vacuum oven at 50° C. The recovered material was analyzed by HPLC and recrystallized from glacial acetic acid (3 mL/gram of crude product) according to the following procedure. The crude dry DKP1 in acetic acid was heated to reflux in an Erlenmeyer flask equipped with a thermometer and a reflux condenser with nitrogen head and outlet connected to a caustic scrubber. After 5 to 10 minutes (to ensure that complete dissolution occurred), the heat was removed and the mixture cooled to a temperature of less than 100° C. Deionized water (1 mL/gram of crude product) was added to the flask and the resulting suspension was cooled to room temperature with stirring over a period of 6-18 hours. The precipitated solid was filtered through a medium porosity sintered glass funnel and washed with deionized water (3×100 mL) and acetone (3×100 mL). The recrystallized wet cake was dried at 50° C. in a vacuum oven.

Example 3

Optimization of Phosphorus Pentoxide Catalyzed Synthesis of DKP1

The dehydrative coupling and cyclization of Cbz-L-lysine to form DKP1 was evaluated as a function of reaction heating time and P$_2$O$_5$ charge. Reactions were carried out using 5%, 7.5% or 10% P$_2$O$_5$ (wt/wt based on Cbz-L-lysine) with various heating times (Table 2). The data indicated that yield and purity were maximized using 7.5% P$_2$O$_5$.

Figure 5:
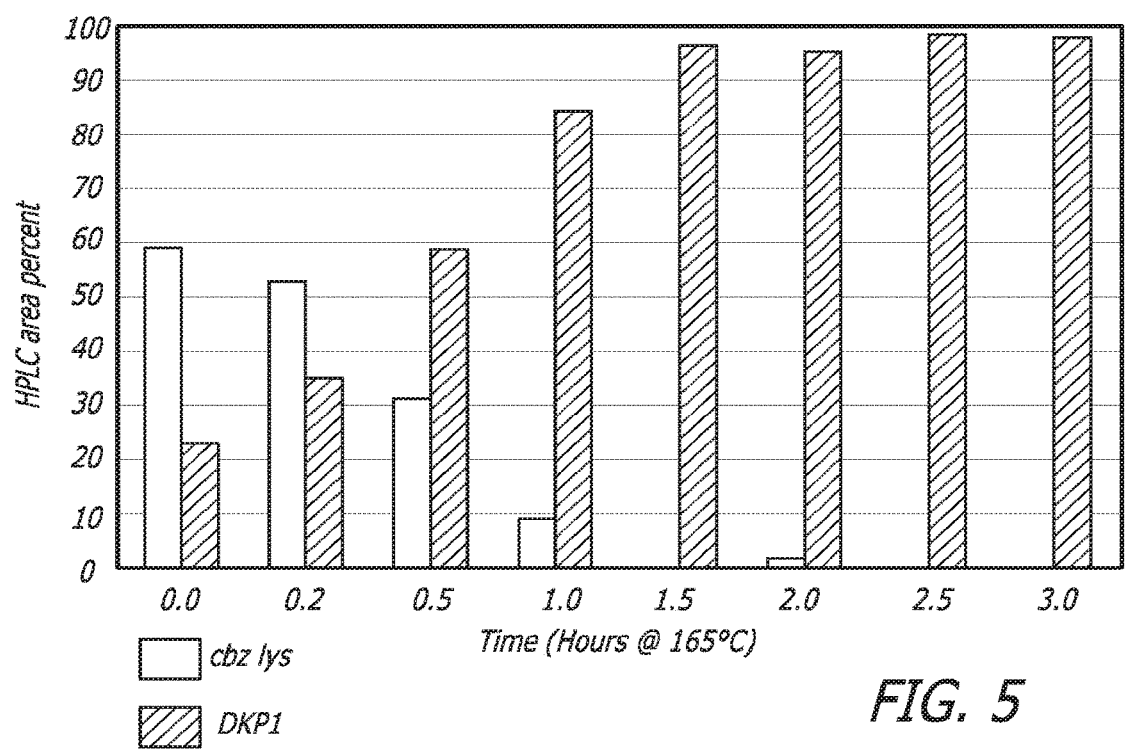
FIG. 5 depicts the conversion of Cbz-L-lysine to DKP1 using the phosphorus pentoxide catalysis methods according to one aspect of the present invention.
Figure 6:
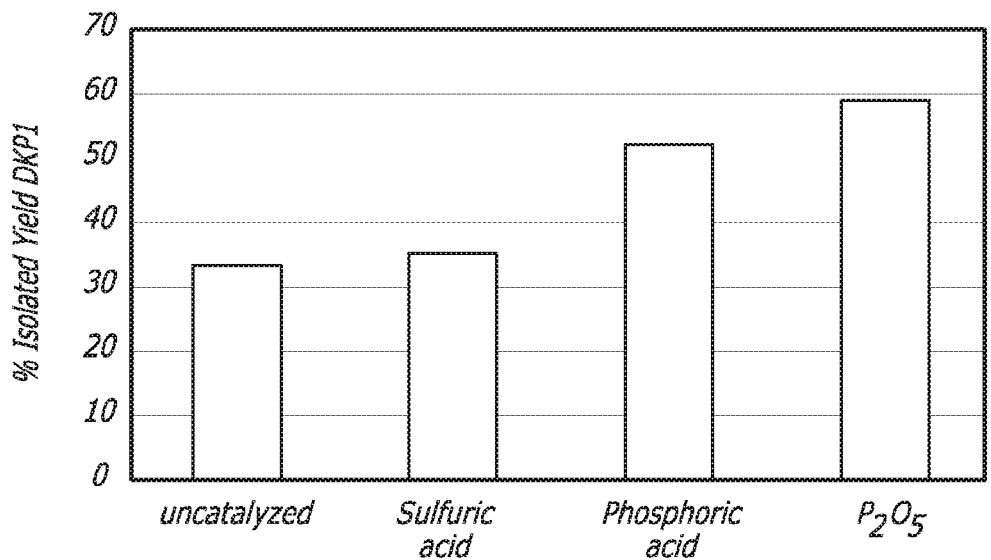
FIG. 6 depicts a comparison of the three catalysts according to one aspect of the present invention.

Subsequent experiments were designed to identify optimal conditions for the 7.5% phosphorus pentoxide catalyzed conversion of Cbz-L-lysine to DKP1. Additionally, these reactions were monitored for the disappearance of Cbz-L-lysine. FIG. 5 shows data obtained from a study in which the Cbz-L-lysine/cresol/P$_2$O$_5$ (7.5%) reaction mixture was monitored for DKP1 formation for 3 hours. During this time the reaction temperature was maintained at 165° C.±5° C. Aliquots (3 mL) were removed at specified times throughout the reaction, quenched with deionized water/methanol, and the product isolated by filtration. HPLC analysis of these samples suggested that the yield of DKP1 reached a maximum after heating for 1 to 3 hours (Table 2). After 4 hours at 165° C.±5° C., a 7-8% decrease in DKP1 yield was observed.

Figure 8:
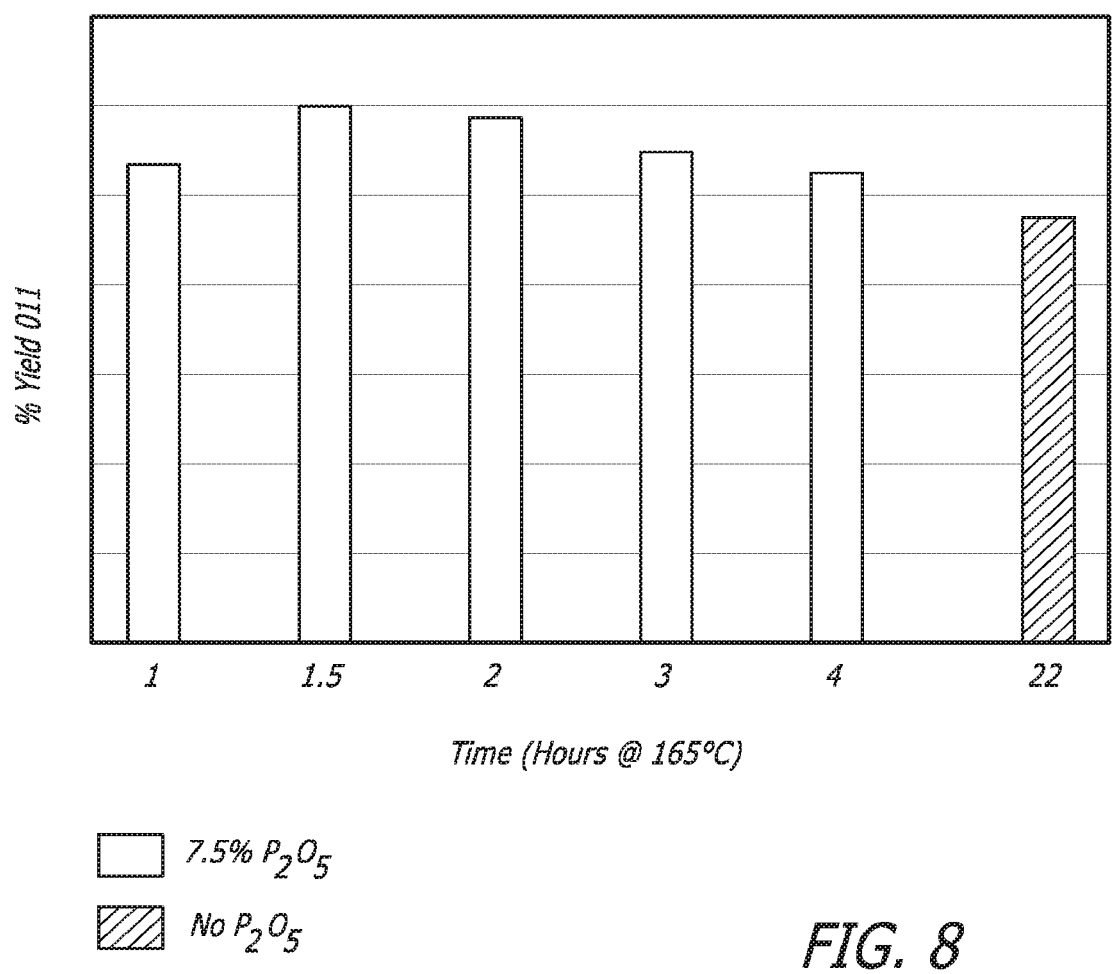
FIG. 8 depicts the overall yield of DKP1 versus time using the phosphorus pentoxide catalyst of the present invention (5 liter scale reaction).

Having identified 1-3 hours as the optimal reaction time, several reactions (100 g scale) were conducted to measure isolated DKP1 yields within this time period. FIG. 8 shows that the maximum DKP1 isolated yield (60.9%) was obtained after 1.5 hours. HPLC analysis showed this material to be >99.5% DKP1. This reaction was repeated with comparable results, namely DKP1 (100.0 area %) was isolated in a 60.3% yield. The reaction was also performed using heat ramps of 4 hours and 6 hours to simulate the large volume heating times. These reactions gave yields of 59.6% and 63.1%, respectively (Table 2).

TABLE 2

Summary of phosphorus pentoxide studies.

| CBZ Lys (g) | % $P_2O_5$ | Time period (hours) | Temp. °C. | Overall Yield (%) | Purity (area %) |
|---|---|---|---|---|---|
| 100 | 10.0 | 0.5 | 165 | 52.90 | 100 |
| 100 | 7.5 | 1 | 165 | 53.30 | 100 |
| 100 | 7.5 | 1.5 | 165 | 60.90 | 100 |
| 100 | 7.5 | 1.5 | 165 | 60.25 | 100 |
| 100 | 7.5 | 2 | 165 | 59.20 | 100 |
| 100 | 7.5 | 2 | 165 | 57.90 | 100 |
| 100 | 10.0 | 2 | 165 | 54.50 | 100 |
| 100 | 7.5 | 3 | 165 | 54.90 | 100 |
| 100 | 10.0 | 3 | 165 | 48.90 | 100 |
| 100 | 7.5 | 4 | 165 | 53.30 | 100 |
| 100 | 7.5 | 4 | 165 | 51.60 | 100 |
| 100 | 7.5 | 1.5* | 165 | 59.60 | 100 |
| 100 | 7.5 | 1.5** | 165 | 63.10 | 100 |

*4 hour heat ramp
**6 hour heat ramp

The optimized conditions (7.5% $P_2O_5$, 165° C., 1.5 hours) were then demonstrated twice at the 5-L scale. Again a 4-hour and a 6-hour ramp were employed to simulate the heating profile employed in production volumes. Both reactions reproduced the results obtained at the 1-L scale. The reactions have overall yields of 58.9% and 58.4% with purity comparable to the current process (99.8%).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar references used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of any and all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for the synthesis of an N-protected 3,6-bis [4-aminoalkyl]-2,5-diketopiperazine comprising heating a solution comprising:
   a. providing an amino acid having a free α-amine group and a protected amine group, and
   b. means for catalyzing dehydrative cyclocondensation of said amino acid.

2. The method of claim 1 wherein said the solution is heated to a target temperature and the target temperature is achieved in about 4-6 hours.

3. The method of claim 1, wherein said solution is heated to a target temperature and the target temperature is maintained for up to 6 hours.

4. The method of claim 1, wherein said solution is heated to a target temperature and wherein said synthesis is substantially complete within about 8 hours of reaching said target temperature.

5. The method of claim 1, wherein the solution is heated to a target temperature of between 160° C. and 170° C.

6. The method of claim 1, wherein said means for catalyzing dehydrative cyclocondensation of said amino acid comprises addition of a catalyst to the solution, wherein said catalyst comprises at least one of sulfuric acid, phosphoric acid, or phosphorus pentoxide.

7. The method of claim 1, wherein the solution further comprises m-cresol, ethylene glycol, propylene glycol, toluene, or xylene.

8. The method of claim 1, further comprising washing a precipitate formed upon incubation with deionized water.

\* \* \* \* \*